United States Patent
Palumbo

(10) Patent No.: US 8,508,737 B2
(45) Date of Patent: *Aug. 13, 2013

(54) SPATIAL FREQUENCY OPTICAL MEASUREMENT INSTRUMENT AND METHOD

(75) Inventor: Perry Palumbo, Fort Collins, CO (US)

(73) Assignee: Hach Company, Loveland, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,629

(22) Filed: Jun. 25, 2012

(65) Prior Publication Data

US 2012/0262717 A1    Oct. 18, 2012

Related U.S. Application Data

(63) Continuation of application No. 12/668,926, filed as application No. PCT/US2008/070055 on Jul. 15, 2008, now Pat. No. 8,208,144.

(60) Provisional application No. 60/950,236, filed on Jul. 17, 2007.

(51) Int. Cl.
*G01N 21/59* (2006.01)
*G01N 21/55* (2006.01)

(52) U.S. Cl.
USPC ......... 356/432; 356/445; 356/448; 250/201.2

(58) Field of Classification Search
USPC ......... 356/335–343, 432–444, 246, 317–318, 356/445, 448; 250/201.1, 201.7, 492.2, 458.1, 250/201.2, 237 R See application file for complete search history.

(56) References Cited

U.S. PATENT DOCUMENTS

| | | | |
|---|---|---|---|
| 3,438,713 A | 4/1969 | Heynacher et al. | |
| 3,771,879 A | 11/1973 | Chambu et al. | |
| 3,879,133 A * | 4/1975 | Mathieu | 356/394 |
| 4,136,953 A | 1/1979 | Klein et al. | |
| 4,350,443 A | 9/1982 | Williamson | |
| 4,750,837 A | 6/1988 | Gifford et al. | |
| 4,846,578 A | 7/1989 | Morita et al. | |
| 4,947,413 A | 8/1990 | Jewell et al. | |
| 4,965,442 A | 10/1990 | Girod et al. | |
| 5,007,737 A * | 4/1991 | Hirleman, Jr. | 356/336 |
| 5,142,648 A | 8/1992 | Fitts et al. | |
| 5,155,558 A | 10/1992 | Tannenbaum et al. | |
| 5,269,937 A * | 12/1993 | Dollinger et al. | 210/656 |
| 5,374,531 A * | 12/1994 | Jensen | 435/7.24 |
| 5,550,632 A | 8/1996 | Harata | |
| 5,621,520 A | 4/1997 | Hoffman | |
| 5,650,632 A | 7/1997 | Coufal et al. | |
| 6,104,490 A * | 8/2000 | Trainer | 356/336 |
| 6,525,302 B2 | 2/2003 | Dowski et al. | |
| 7,792,423 B2 | 9/2010 | Raskar et al. | |
| 2008/0037004 A1 * | 2/2008 | Shamir et al. | 356/73 |

* cited by examiner

*Primary Examiner* — Sang Nguyen
(74) *Attorney, Agent, or Firm* — Ference & Associates LLC

(57) ABSTRACT

A spatial frequency optical measurement instrument is provided according to the invention. The instrument includes a spatial frequency mask positioned in a light path and configured to encode light with spatial frequency information, a light receiver positioned to receive the light encoded with the spatial frequency information, wherein the light encoded with the spatial frequency information has been interacted with a sample material, and a processing system coupled to the light receiver and configured to determine a change in the spatial frequency information due to the interaction of the light with the sample material.

6 Claims, 11 Drawing Sheets

SPATIAL FREQUENCY OPTICAL MEASUREMENT INSTRUMENT AND METHOD

CROSS REFERENCE TO RELATED APPLICATIONS

This application is a continuation of U.S. patent application Ser. No. 12/668,926, entitled "SPATIAL FREQUENCY OPTICAL MEASUREMENT INSTRUMENT AND METHOD", filed Jan. 13, 2010, now U.S. Pat. No. 8,208,144 which is a national stage entry of PCT/US08/70055, filed Jul. 15, 2008, which in turn claims priority to U.S. Provisional Patent Application No. 60/950,236, filed Jul. 17, 2007; the contents of these applications are incorporated by reference in their entirety as set forth fully herein.

BACKGROUND OF THE INVENTION

1. Field of the Invention

The invention is related to the field of optical measurement instruments, and in particular, to a spatial frequency optical measurement instrument and method.

2. Statement of the Problem

A turbidimeter or nephelometer is an instrument used for the determination of the concentration and/or size of particles in a suspension media. A nephelometer generally refers to an optical instrument for detecting and/or measuring suspended particulates in a liquid or gas colloid. In contrast, a turbidimeter generally refers to an optical instrument for detecting and/or measuring particulate matter in water. Consequently, the suspension media can comprise water.

In the prior art, light is projected through a sample material. The sample material comprises a suspension media and an unknown concentration of particles. The particles within the suspension scatter the impinging light by a complex interaction of reflection, diffraction, and refraction. A portion of the incident light is scattered from the particles and is received by a detector. The detector is commonly a silicon diode or other photosensitive device, typically positioned approximately 90 degrees to the incident light source.

In order to quantify the amount of particles within the suspension media, a comparison must be made of the received scattered light to a scattered light level obtained using a similar suspension media of known particulate concentration. Subsequently, unknown particulate concentrations can be compared to known calibration values and can be determined by estimation or extrapolation from the calibration values.

FIG. 1 shows a prior art turbidimeter/nephelometer. A light source 1 emits light into a sample material 4 contained within a sample chamber 3. Optical components may collimate and/or focus the light toward the sample chamber 3. Light from the light source 1 can either propagate through the sample material 4 unimpeded or can interact with the sample material 4 by impinging on particles in the material. Light impinging on a particle can scatter in multiple directions, including a backward direction, a forward direction, and can scatter sideways, such as along a path substantially at ninety degrees to the incident beam. Light scattered to the side may impinge on a detector 2a. Unscattered light may be received by a second detector 2b that can be used to determine an intensity of the light from the light source 1. The detector 2a converts photon energy into an electrical signal by means of a photoelectric effect. The electrical signal, usually weak or low in signal strength, can be amplified and can subsequently be processed in a processing system in order to determine a turbidity of the sample material 4. The determined turbidity can be output to a meter or other useful indicator.

Optical measurement instruments used to measure scattering effects rely almost exclusively on a method of measurement that assesses changes in intensity of light or radiant energy. The light or radiant energy can be either transmitted through or reflected from the sample. The measurement of scattering can be used for a determination of the particulate concentration of the scattering constituent or can be used for a determination of a surface condition/finish of the sample.

Prior art methods for determination of turbidity by nephelometric means rely on an amplitude detection of the scattered signal from a turbid sample. The prior art measures only the intensity of the received light.

The prior art has drawbacks. In the prior art, the signal values corresponding to the received light intensity are very small for low concentrations of particles and are ideally zero when no particles are present in the suspension media. Consequently, the limit of detection is a function of a signal-to-noise ratio (SNR) of the detector, the intensity of the light source, and the amount of stray light impinging on the detector, wherein the stray light is not associated with the particles in the suspension media. In addition, the accuracy of a prior art nephelometric assay is further degraded by drift or changes in the intensity of the light source or sensitivity of the detector due to temperature changes or wear. In the prior art, the accuracy is further degraded by any light absorption by the suspension media, since prior art methods rely on absolute intensity measurements or on a ratio of the intensity of the received scattered light to the intensity of the emitted light. Changes in the light intensity impinging upon the detector, not associated with the measure of turbidity, produces an error in the measured response. Consequently, any changes in color or absorption of the suspension media can also result in false determination of the concentration of particles in a suspension, since this also results in a change in the absolute measure of the intensity of the light.

Prior art methods have been devised to reduce or counter these effects, such as dual beam, dual wavelength, or ratio methods, but limitations arise due to the increased cost and complexity of adding secondary or alternate light sources and detectors such as non-uniform degradation of surfaces due to bubbles, biological films, or dirt.

There remains a need for a nephelometric particle assay that does not depend on the explicit quanta/intensity of received light.

Aspects

One aspect of the invention includes a spatial frequency optical measurement instrument, comprising:

a spatial frequency mask positioned in a light path and configured to encode light with spatial frequency information;

a light receiver positioned to receive the light encoded with the spatial frequency information, wherein the light encoded with the spatial frequency information has been interacted with a sample material; and a processing system coupled to the light receiver and configured to determine a change in the spatial frequency information due to the interaction of the light with the sample material.

Preferably, the instrument, with interacting the light with the sample material comprising substantially passing the light through the sample material.

Preferably, the instrument, with interacting the light with the sample material comprising substantially reflecting the encoded light off of the sample material.

Preferably, one or more optical components configured to define a spatial frequency image of the spatial frequency mask at the light receiver, with the spatial frequency image substantially including the spatial frequency information.

Preferably, a light source configured to emit the light along the light path.

Preferably, the light source further comprises a powered light source.

Preferably, the light source further comprises an ambient light source.

Preferably, the spatial frequency mask being located before the sample material and encoding light that has not interacted with the sample material.

Preferably, the spatial frequency mask being located after the sample material and encoding light that has interacted with the sample material.

Preferably, the spatial frequency mask comprises light blocking and light transmitting regions that encode the spatial frequency information.

Preferably, the spatial frequency mask comprises a series of spatially varying blocking and light transmitting regions that encode the spatial frequency information.

Preferably, the spatial frequency mask comprises a series of apertures that encode the spatial frequency information.

Preferably, the spatial frequency mask comprises a series of spatially varying apertures that encode the spatial frequency information.

Preferably, a light path length through the sample material can be varied in order to vary the change in spatial frequency information.

Preferably, the light path includes one or more excursions through or reflections from the sample material.

Preferably, the light path includes one or more excursions through or reflections from the sample material and wherein the number of excursions or reflections can be varied in order to vary the spatial frequency information.

Preferably, the spatial frequency information being substantially independent of the intensity or composition of the light.

Preferably, the change in the spatial frequency information includes a change to a content or organization of the spatial frequency information.

Preferably, the change in the spatial frequency information includes a change to one or more of a line, an edge, a bar pattern, a sinusoidal pattern, or a point function of the spatial frequency information.

Preferably, determining the change in the spatial frequency information comprises determining a change in the spatial frequency information from a predetermined standard.

Preferably, determining the change in the spatial frequency information comprises determining a change in contrast in the spatial frequency information from a predetermined contrast standard.

Preferably, the processing system further determines a particulate concentration in a media of the sample material based on the change in the spatial frequency information.

Preferably, determining the particulate concentration further comprises comparing the spatial frequency information to one or more predetermined particulate concentration images and interpolating and/or extrapolating a particulate concentration value from the one or more predetermined particulate concentration images.

Preferably, the processing system further determines one or more surface characteristics of the sample material.

Preferably, determining the one or more surface characteristics further comprises comparing the spatial frequency information to one or more predetermined surface images and interpolating and/or extrapolating the one or more surface characteristics from the one or more predetermined surface images.

Preferably, a first portion of the encoded light is reflected onto a first light receiver without interacting with the sample material and wherein a second portion of the encoded light is interacted with the sample material and wherein the second portion of the encoded light is compared to the first portion.

Preferably, the light comprising a first light portion interacting with the spatial frequency mask and the sample material to form a spatial frequency image and with the light further comprising a second light portion interacting with a predetermined standard material to form a predetermined standard image, wherein the change in the spatial frequency information comprising a difference between the spatial frequency image and the predetermined standard image.

Another aspect of the invention comprises a spatial frequency optical measurement method, comprising:

encoding light with spatial frequency information;
interacting the light with a sample material; and
determining a change in the spatial frequency information due to the interaction of the light with the sample material.

Preferably, the method further comprises interacting the light with a spatial frequency mask positioned in a light path.

Preferably, the method further comprises interacting the light with a spatial frequency mask positioned in a light path, with the spatial frequency mask comprising light blocking and light transmitting regions that encode the spatial frequency information.

Preferably, the method further comprises interacting the light with a spatial frequency mask positioned in a light path, with the spatial frequency mask comprising a series of spatially varying light blocking and light transmitting regions that encode the spatial frequency information.

Preferably, the method further comprises interacting the light with a spatial frequency mask positioned in a light path, with the spatial frequency mask comprising a series of apertures that encode the spatial frequency information.

Preferably, the method further comprises interacting the light with a spatial frequency mask positioned in a light path, with the spatial frequency mask comprising a series of spatially varying apertures that encode the spatial frequency information.

Preferably, the method further comprises interacting the light with the sample material comprising substantially passing the light through the sample material.

Preferably, the method further comprises interacting the light with the sample material comprising substantially reflecting the encoded light off of the sample material.

Preferably, the method further comprises a light path length through the sample material can be varied in order to vary the change in spatial frequency information.

Preferably, the method further comprises a light path includes one or more excursions through or reflections from the sample material.

Preferably, the method further comprises a light path includes one or more excursions through or reflections from the sample material and wherein a number of excursions or reflections can be varied in order to vary the change in spatial frequency information.

Preferably, the method further comprises spatial frequency information being substantially independent of the intensity or composition of the light.

Preferably, the method further comprises the change in the spatial frequency information including a change to a content or organization of the spatial frequency information.

Preferably, the method further comprises the change in the spatial frequency information including a change to one or more of a line, an edge, a bar pattern, a sinusoidal pattern, or a point function of the spatial frequency information.

Preferably, the method further comprises determining the change in the spatial frequency information comprising determining a change in the spatial frequency information from a predetermined standard.

Preferably, the method further comprises determining the change in the spatial frequency information comprising determining a change in contrast in the spatial frequency information from a predetermined contrast standard.

Preferably, the method further comprises the processing system further determining a particulate concentration in a media of the sample material based on the change in the spatial frequency information.

Preferably, the method further comprises determining the particulate concentration further comprising:
comparing the spatial frequency information to one or more predetermined particulate concentration images; and
interpolating and/or extrapolating a particulate concentration value from the one or more predetermined particulate concentration images.

Preferably, the method further comprises the processing system further determining one or more surface characteristics of the sample material based on the change in the spatial frequency information.

Preferably, the method further comprises determining the one or more surface characteristics further comprising:
comparing the spatial frequency information to one or more predetermined surface images; and
interpolating and/or extrapolating the one or more surface characteristics from the one or more predetermined surface images.

Preferably, the method further comprises a first portion of the encoded light is reflected onto a first light receiver without interacting with the sample material and wherein a second portion of the encoded light is interacted with the sample material and wherein the second portion of the encoded light is compared to the first portion.

Preferably, the method further comprises the light comprising a first light portion interacting with the spatial frequency mask and the sample material to form a spatial frequency image and with the light further comprising a second light portion interacting with a predetermined standard material to form a predetermined standard image, wherein the change in the spatial frequency information comprising a difference between the spatial frequency image and the predetermined standard image.

Another aspect of the invention comprises a spatial frequency optical measurement method, comprising:
interacting light with a sample material;
reflecting and encoding the light with spatial frequency information; and
determining a change in the spatial frequency information due to the interaction of the light with the sample material.

Preferably, the method further comprises reflecting and encoding the light comprising interacting the light with a reflective spatial frequency mask positioned in a light path.

Preferably, the method further comprises reflecting and encoding the light comprising interacting the light with a reflective spatial frequency mask positioned in a light path, with the reflective spatial frequency mask comprising light reflecting and non-reflecting regions that encode the spatial frequency information.

Preferably, the method further comprises reflecting and encoding the light comprising interacting the light with a reflective spatial frequency mask positioned in a light path, with the reflective spatial frequency mask comprising a series of spatially varying light reflecting and non-reflecting regions that encode the spatial frequency information.

Preferably, the method further comprises reflecting and encoding the light comprising interacting the light with a reflective spatial frequency mask positioned in a light path, with the reflective spatial frequency mask comprising a series of apertures that encode the spatial frequency information.

Preferably, the method further comprises reflecting and encoding the light comprising interacting the light with a reflective spatial frequency mask positioned in a light path, with the reflective spatial frequency mask comprising a series of spatially varying apertures that encode the spatial frequency information.

Preferably, the method further comprises interacting the light with the sample material comprising substantially passing the light through the sample material.

Preferably, the method further comprises a light path length through the sample material can be varied in order to vary the change in spatial frequency information.

Preferably, the method further comprises a light path includes one or more excursions through the sample material.

Preferably, the method further comprises a light path includes one or more excursions through the sample material and wherein a number of excursions can be varied in order to vary the spatial frequency information.

Preferably, the method further comprises spatial frequency information being substantially independent of the intensity or composition of the light.

Preferably, the method further comprises the change in the spatial frequency information including a change to a content or organization of the spatial frequency information.

Preferably, the method further comprises the change in the spatial frequency information including a change to one or more of a line, an edge, a bar pattern, a sinusoidal pattern, or a point function of the spatial frequency information.

Preferably, the method further comprises determining the change in the spatial frequency information comprising determining a change in the spatial frequency information from a predetermined standard.

Preferably, the method further comprises the change in the spatial frequency information comprising determining a change in contrast in the spatial frequency information from a predetermined contrast standard.

Preferably, the method further comprises the processing system further determining a particulate concentration in a media of the sample material based on the change in the spatial frequency information.

Preferably, the method further comprises the particulate concentration further comprising:
comparing the spatial frequency information to one or more predetermined particulate concentration images; and
interpolating and/or extrapolating a particulate concentration value from the one or more predetermined particulate concentration images.

Preferably, the method further comprises the processing system further determining one or more surface characteristics of the sample material based on the change in the spatial frequency information.

Preferably, the method further comprises the one or more surface characteristics further comprising:
comparing the spatial frequency information to one or more predetermined surface images; and
interpolating and/or extrapolating the one or more surface characteristics from the one or more predetermined surface images.

Preferably, the method further comprises the light comprising a first light portion interacting with the spatial frequency mask and the sample material to form a spatial frequency image and with the light further comprising a second light portion interacting with a predetermined standard material to form a predetermined standard image, wherein the change in the spatial frequency information comprising a difference between the spatial frequency image and the predetermined standard image.

DESCRIPTION OF THE DRAWINGS

The same reference number represents the same element on all drawings. It should be understood that the drawings are not necessarily to scale.

DETAILED DESCRIPTION OF THE INVENTION

FIGS. 2-12 in the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
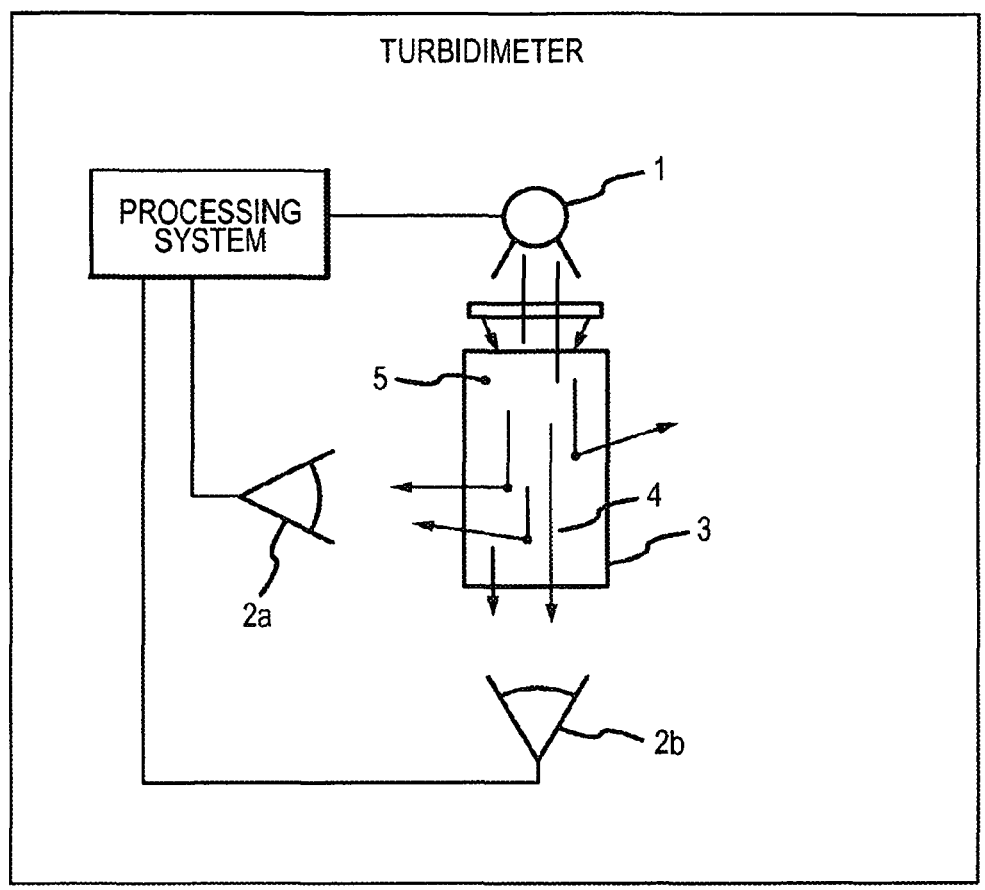
FIG. 1 shows a prior art turbidimeter/nephelometer.
Figure 2:
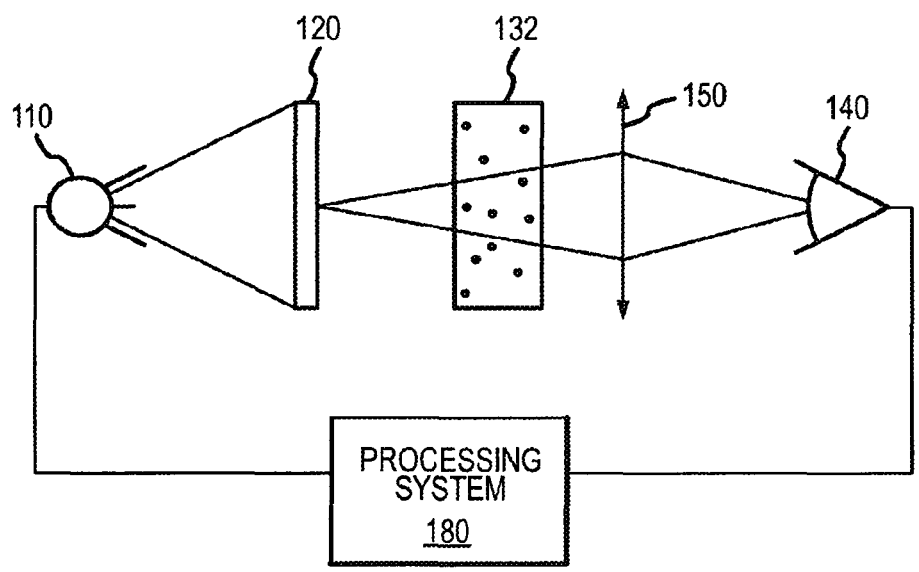
FIG. 2 shows a spatial frequency optical measurement instrument according to an embodiment of the invention.

FIG. 2 shows a spatial frequency optical measurement instrument 100 according to an embodiment of the invention. The spatial frequency optical measurement instrument 100 uses a spatial frequency differentiation in order to determine a particulate concentration of a test sample and produce a particulate concentration value in one embodiment. In another embodiment, the spatial frequency optical measurement instrument 100 uses the spatial frequency differentiation in order to determine one or more surface characteristics of a test sample. The spatial frequency optical measurement instrument 100 is independent of light intensity.

The instrument 100 can comprise a nephelometer. The instrument 100 can comprise a turbidimeter. However, it should be understood that the instrument 100 can comprise any manner of instrument that measures or quantifies interaction of light with a test sample.

The optical measurement instrument 100 includes a light source 110, a sample material 132, a light receiver 140, and a processing system 180. The optical measurement instrument 100 further includes a spatial frequency mask 120. The processing system 180 is connected to the light receiver 140. The processing system 180 can further be connected to any manner of user interface (not shown), including user input and/or output devices.

The sample material 132 can comprise any material, including a solid, a liquid, a gas, or a gel, for example. The sample material 132 can comprise a first material including an amount of a second material included in the first material, such as a suspension in a gas, liquid, gel, etc. The sample material 132 can comprise a material including an outer surface.

The spatial frequency optical measurement instrument 100 can determine a particulate concentration in the sample material 132, such as a particulate concentration in a liquid, gas, gel, etc. Alternatively, the spatial frequency optical measurement instrument 100 can determine one or more surface characteristics of a solid or at least partially solid sample material 132.

The light source 110 comprises a light source for performing an optical measurement. The light source 110 can comprise any electromagnetic radiant element and is not limited to the visual portion of the electromagnetic spectrum. The light source 110 can emit light of any composition, such as including one or more specific frequencies, wavelengths, colors, etc. The light source 110 can comprise a powered light source or can comprise ambient or naturally occurring radiant energy. The light source 110 is positioned to emit light through or reflect light from the sample material 132.

A determination of turbidity by quantifying the change in spatial frequency response is not limited to visible wavelengths. Indeed, UV, Visible, Infrared and others wavelengths may be used. They can be used alone, in combination, or in aggregate in order to further enhance or modify the response to a specific particulate within the sample material 132. The light can further be chosen in order to be able to filter out or otherwise reject light other than that wavelength at which the spatial evaluation is to be determined. Ambient light can therefore be negated.

The light can be substantially collimated, focused, or otherwise directed toward sample material 132, such as by one or more optical components 150. The one or more optical components 150 can include components before, after, or both before and after the sample material 132.

The sample material 132 can be self-contained or can be held in a sample chamber 130. When useful or necessary to contain the sample material 132, a sample chamber 130 is constructed of a material, transparent at the wavelength(s) of interest. The sample material 132 can comprise a gaseous, liquid, solid, or semi-solid (gel) material. The sample material 132 can include particles, such as suspended particles, for example.

Light emitted from the light source 110 is interacted with the sample material 132. The light is directed along a light path through the test chamber 130 and consequently through the sample material 132 (assuming that the sample material 132 is present). Alternatively, the light can be substantially reflected from the sample material 132, such as in the case of an at least partially solid sample material 132. Interacting the light with the sample material 132 can comprise any manner of interaction.

Light is scattered by particles 101 in the sample material 132. The sample material 132 can therefore result in scattered light that is scattered away from the light path by particles 101 in the test chamber 130 at various forward and backward directions, as shown in the figure. The sample material 132 can further result in some of the light remaining as unscattered light that propagates through the test chamber 130. This unscattered light is directionally unaffected.

The spatial frequency mask 120 comprises a component that encodes spatial frequency information into the light. The light can be encoded either before or after passing through the sample material 132, as in some embodiments, the light can be encoded between excursions through the sample material 132. To that end, the spatial frequency mask 120 may comprise a series of light blocking and light transmitting regions that encode the spatial frequency information, including spatially varying light blocking and light transmitting regions. Alternatively, the spatial frequency mask 120 can comprise a series of apertures 123, including spatially varying apertures 123. The series of apertures in one embodiment comprises a series of slots (see FIG. 3). As a result, the spatial frequency mask 120 encodes the light by forming an image including regions of light and including regions of substantially no light. A resulting spatial variation can be used to determine one or more characteristics of the sample material 132.

When particulate is present in the sample material 132, then the spatial frequency information is changed by interaction with the test sample 132, i.e., the encoded light is "confused" by the interaction with the test sample 132. The interaction can result in changes to the content or organization of the spatial frequency information, or both. Consequently, the particulate scatters a portion of the impinging light and a portion of the scattered light subsequently propagates along a light path toward the light receiver 140. The degree to which the spatial frequency image is changed is related to the amount of particulate matter present in the sample material 132. The degree of change in turn affects the quality of the spatial frequency image formed at the light receiver 140. To that end, the spatial frequency image is formed at the light receiver 140 by the one or more optical components 150.

At least some of the scattered light can be detected and received by the light receiver 140. Light that is received by the light receiver 140 can be used to determine a particulate concentration in the sample material 132. The received light comprises an image formed of the encoded, confused spatial frequency information. The spatial frequency image at the light receiver 140 can be compared to one or more predetermined particulate concentration images. A particulate value can subsequently be interpolated and/or extrapolated from the one or more predetermined particulate concentration images.

The particulate value can comprise any measure of particulate concentration. The particulate value can comprise a turbidity value or nephelometric measurement. The particulate value can comprise a measurement of one or more surface characteristics, including surface roughness or surface texture, for example.

The light receiver 140 generates a signal related to the received light and that is compatible with the processing system 180. However, unlike in the prior art, the light receiver 140 does more than quantify a received light intensity. Instead, the light receiver 140 generates a measurement signal encoded with the spatial frequency information that is changed in relationship to the particulate concentration or content of the sample material 132. Specifically, the measurement signal contains spatial information that can be encoded within the image as a contrast, sharpness, or abruptness of change between adjacent light and dark portions of the image.

The light receiver 140 in some embodiments is positioned out of a light path emanating from the light source 110. The light receiver 140 can be substantially at a right angle from the light path or can be positioned substantially obliquely from the light path. Consequently, the light receiver 140 is positioned to receive scattered first light from the test chamber 130. Alternatively, the light receiver 140 can be positioned substantially opposite the light source 110 and therefore can receive light that has passed through the test chamber 140 (see FIG. 9).

An advantage of the described method is realized as a result of the turbidity measurement being made in transmission rather than by measurement of scattered light at 90 degrees to an incident, illumination beam. In the prior art, when the particle count is low or when the view volume is small, (the view volume defined as the intersecting volume formed by the incident beam of illuminating radiation and the field of view of the detector), then the signal may be less than the noise floor or detection limit and improvement can be realized only by increasing the intensity of the illumination beam or by increasing the system gain. Since the measurement of the present invention is one of spatial information content, the intensity may be selected to always exceed the detection limit of the electrical system and yet to minimize the total required power. There is no need for a power hungry high intensity light source. Overall, the total power required to make a turbidity measurement can be dramatically reduced, since the transmission through the optical measurement instrument 100 can easily exceed 98%. However, when received light is measured at 90 degrees from the source, the signal efficiency is quite low, less than 0.1%, due to the small percentage of the incident energy that is scattered from particles and received. This is compensated for in prior art nephelometric systems by either increased detection gain, (which also increases the noise signal), increased incident power, or both.

Figure 3:
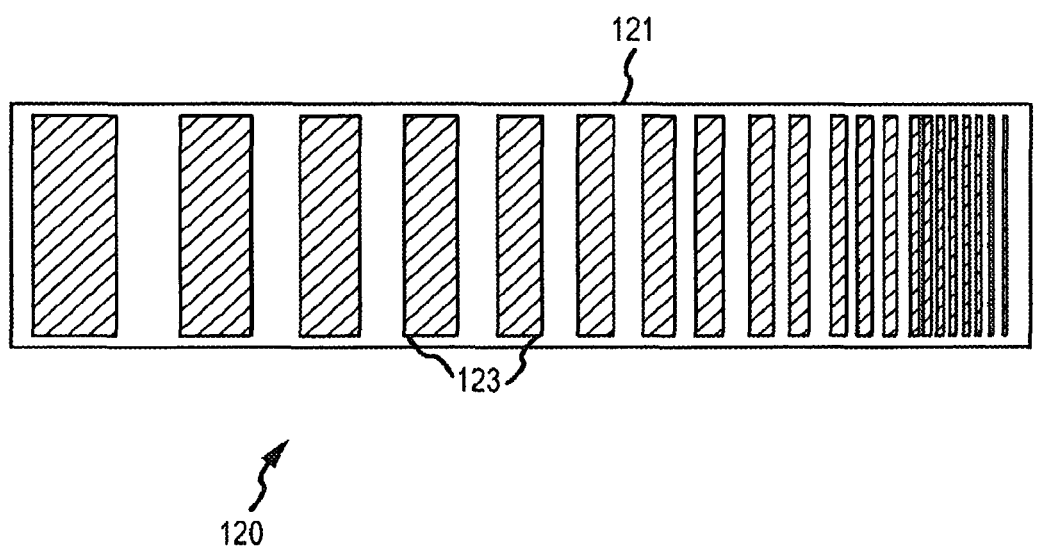
FIG. 3 shows a spatial frequency mask according to an embodiment of the invention.

FIG. 3 shows the spatial frequency mask 120 according to an embodiment of the invention. The spatial frequency mask 120 in this embodiment comprises a substantially planar body 121 and a series of apertures 123. The apertures 123 let light selectively pass through the spatial frequency mask 120. The apertures 123 are decreasing in width and separation across the spatial frequency mask 120, such as from left to right in the figure. The apertures 123 are correspondingly increasing in frequency in the same direction, i.e., as the apertures 123 decrease in size they are located closer and closer together. The series of apertures 123 therefore create a series of light transmitting regions separated by opaque regions, wherein the regions are spatially increasing in frequency and decreasing in size. Consequently, light encoded by the spatial frequency mask 120 can be processed to determine turbidity as consequence to the interaction of the encoded light with the sample material 132. In other embodiments, the spatial frequency mask 120 may be alternately reflective and/or absorbing, instead of transmitting and opaque.

In some embodiments, the apertures 123 comprise slots or openings through the body 121. In some embodiments, the apertures 123 comprise substantially rectangular slots, as shown. However, other shapes are contemplated and are within the scope of the description and claims.

In still other embodiments the series of apertures may be replaced by a single transmitting/opaque aperture or a single reflective/absorbing aperture, wherein the spatial frequency information is encoded within the transition from a transmitting to opaque region or a reflective to absorbing edge, for example.

A square wave pattern of a fundamental frequency, i.e. a pattern wherein the transitions from one level to an adjacent level are abrupt at regular intervals, can be simulated as a sum of sinusoidal wave forms as of the odd harmonics x(t'), comprising:

$$x(t') = 2\left[\frac{4}{\pi}\left(\sum_h \frac{1}{h}\sin(h \cdot 2 \cdot \pi \cdot t' \cdot \text{Hz})\right)\right] \quad (1)$$

Where the (t') term represents time, the (Hz) term represents the fundamental frequency, and the odd harmonics are the vector h=1, 3, 5, . . . to infinity. Therefore, a single abrupt edge can act as spatial frequency mask 120 composed of an infinite number of frequencies. Consequently, an infinite amount of spatial information can be used to encode light for the determination of the Spatial Frequency Response (SFR) of an optical system or instrument without the encoding mask needing to comprise a pattern.

The body 121 can comprise a substantially light opaque material wherein the apertures 123 are formed in the body 121. Alternatively, the body 121 can comprise a series of substantially light absorbing and substantially light reflecting regions, with the light absorbing and light reflecting regions forming the spatial frequency mask 120. Alternatively, the body 121 can comprise a substantially translucent or transparent material and some manner of light opaque material can be used to form apertures 123. For example, the spatial frequency mask 120 can comprise a substantially clear glass or plastic with a light opaque film positioned on the body 121, wherein the light-transmissive apertures 123 are formed in the film. Alternatively, the spatial frequency mask 120 can comprise a substrate wherein dark and light regions are printed, stamped, or otherwise deposited or formed on the substrate. However, it should be understood that the spatial frequency mask 120 can be formed of other materials and structures, and such materials and structures are contemplated and are within the scope of the description and claims.

Referring again to FIG. 2, the processing system 180 is connected to the light receiver 140 and receives an electrical measurement signal therefrom. The measurement signal is related to the spatial frequency encoded light that is received from interaction with sample material 132. The processing system 180 processes the measurement signal to generate a measurement value. The measurement value in some embodiments, in an application of nephelometry, comprises a quantification of the particulate concentration 101 in the sample material 132, i.e., a turbidity measurement.

The processing system 180 in some embodiments receives user inputs and conducts a measurement. This includes turning on and off the light source 110, receiving the measurement signal from the light receiver 140, and calculating the measurement value from the measurement signal. The processing system 180 can further generate an output of the measurement value, such as by generating a display, for example. The display can comprise any manner of display.

It should be understood that the optical measurement instrument 100 can include any manner of additional optical devices positioned between the various optical components. For example, the optical devices can include lenses, filters, apertures, collimators, and reflectors/mirrors. However, other optical devices are also contemplated and are within the scope of the description and claims.

During operation, the light receiver 140 receives an image of spatial frequency mask 120. The image of spatial frequency mask 120 comprises light that has passed through or reflected from the spatial frequency mask 120 and that has further passed through and interacted with the sample material 132. Alternatively, the light can pass through the sample material 132 multiple times, such as through the use of mirrors, reflectors, etc. The image corresponds at least somewhat to the spatial frequency mask 120. However, the particle concentration or turbidity of the sample material 132 will affect the spatial frequency content of the image. As a result, the image impinging upon the light receiver 140 will comprise a SFR of instrument 100. The SFR of the instrument, also known as a Modulation Transfer Function (MTF), will vary with the spatial frequency content of the image and therefore the particle concentration or turbidity of sample material 132. The MTF is therefore a function of the turbidity and can be used to quantify the particulate concentration of sample material 132. The processing system 180 can assay a change in the MTF from a stored value representing the sample material media absent suspended particles, for example.

Figure 4:
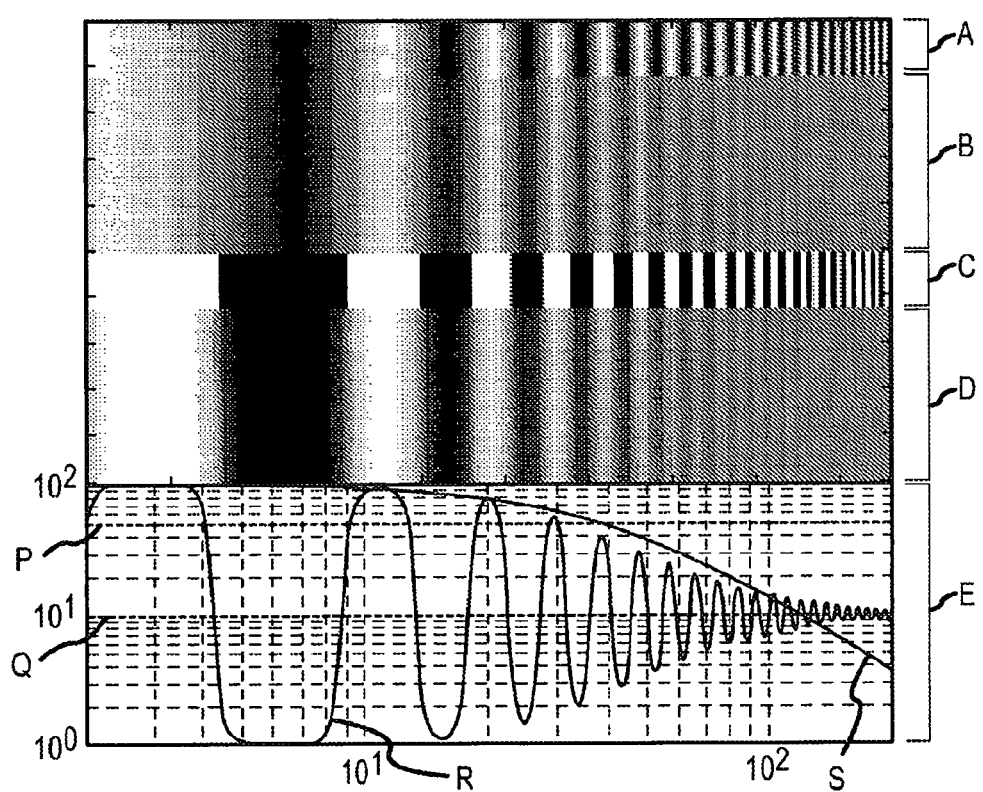
FIG. 4 comprises a combination graph that includes various modulated images and a corresponding SFR image received from the optical measurement instrument.

FIG. 4 comprises a combination graph that includes various modulated images and a corresponding SFR image received from the optical measurement instrument 100. Portion C shows an example of a spatial frequency encoding mask of a block style, including black and white blocks having straight, solid edges. Portion C uses a spatial frequency mask 120 that comprises black and white, absorbing and reflecting (or clear and opaque) regions featuring well defined, high contrast edges or transitions from black to white. The spatial frequency encoding mask of portion C does not exhibit any blurring, i.e. spatial frequencies are clearly separated. The spatial frequency measurement instrument 100, without any turbidity present, will produce an image that is substantially equal to the spatial frequency mask 120, including well defined edges and well defined light regions and dark regions.

Portion A shows a spatial frequency encoding mask employing a sinusoidal distribution of light and dark regions. The pattern matches that of portion C, but does not feature high contrast edges and instead varies between black and white in a sinusoidal fashion. However, the sinusoidal pattern still comprises light and dark regions that vary from clear to opaque, black to white, or from reflecting to absorbing. Consequently, a processing routine of the processing system 180 can calculate a SFR that features spatial information in a form of low contrast edges, provided the encoded spatial frequency information is diverse and high in content.

Portion D shows an example of a spatial frequency encoding mask image of Portion C with confusion of spatial information due to interaction of sample material with the encoded light at a significant or measurable turbidity level. It can be seen that the largest black and white regions of portion D are fairly well defined and quantifiable. However, the smallest black and white regions on the right of the figure have very little contrast and the edges between regions are significantly blurred or confused by the turbidity of the sample material. As a result, the processing system 180 will likely not be able to discriminate between the small, closely spaced black and white regions, i.e. the high frequency spatial information is unrecoverable. Therefore, a turbidity measurement corresponds to a level of SFR that can be achieved by the instrument 100. The change in the SFR in Portion D can be quantified as a turbidity measurement.

Portion B shows a sine pattern style spatial frequency encoding mask image of Portion A for an example turbidity level. Portion B may be a sinusoidal pattern image equivalent to Portion D. Because the image in Portion D has spatial information that has been confused by the particles 101 of the sample material 132, the sinusoidal spatial frequency encoding mask image of Portion B likewise shows a similar degradation to the high spatial frequency information. Portion B therefore shows a similar loss of spatial frequency information as is seen in Portion D.

Portion E of FIG. 4 comprises a line graph that illustrates a SFR of the optical measurement instrument 100 as a percent MTF on the y-axis. Line P, Portion E in FIG. 4 graph reflects a 50% MTF level determination and line Q reflects a 10% MTF level determination. Line R shows the spatial frequency response of the system for a turbid sample material. Line S shows the derived % MTF. The spatial resolution or spatial frequency response is read along the x-axis in line pairs per unit distance (i.e., LP/mm, for example) and is approximately 40 LP/mm at the 50% MTF level and 120 LP/mm at the 10% MTF level for the turbid sample.

Introduction of particles into a sample material 132, whether fluid or gaseous in nature, scatters light and confuses the spatial information contained within the encoded light as it is transmitted through and interacts with the sample material 132. The confusion of spatial frequencies of the encoded light by the particles 101 of the sample material 132 invariably reduces the contrast of the image generated by the spatial frequency mask 120 at the highest spatial frequencies. This is true even for small changes of turbidity and toward the low spatial frequencies. Therefore, a determination of the turbidity of the sample can be made through the evaluation or comparison of the spatial frequency response of the optical measurement instrument 100 in the presence or absence of particles.

If the optical measurement instrument 100 includes a sample material 132, then the % MTF is a result of the convolution of a spatial frequency response of the instrument and the function of confusion of the sample material. Attenuation of the light due to the absorption by the suspension media or color of the suspension media affects only the amplitude/intensity of the light without change to the content of the encoded spatial frequency information. Advantageously, the % MTF is not affected by changes in intensity of the light source, by changes in gain of the detector, nor attenuation by the suspension media by absorption.

The sensitivity of the turbidity measurement by spatial frequency response can be modified with a change in the traversed distance by the encoded light through sample material 132. This can be accomplished by increasing/decreasing a light path distance or by means of multiple/fewer excursions of the spatially encoded light through sample material 132. In this manner, more or fewer particles are introduced into light path for a given concentration of particles 101. A longer path length increases the sensitivity to the presence or concentration of particles 101. Conversely, a shorter path length lowers the sensitivity and can be used where higher concentration of particles is present. An optimal path length can therefore be chosen in order to obtain the best sensitivity over the nephelometric range of interest.

All optical systems have finite spatial resolving power. This finite resolving power or resolution is due to light scatter and position errors in the optical surfaces. Finite resolution is also a result of optical aberrations and diffraction effects of apertures and limiting edges that comprise the holding means for the optical elements. One assay of the performance of an optical system is the ability of the optical system to image and resolve fine detail within the image. One method for the determination of imaging resolution is by evaluation of the contrast between line pairs of known separation by use of resolution targets or line pair targets, such as the USAF 1951 Test Pattern. A resolution target generally comprises alternating black and white, clear and opaque, or reflecting and absorbing lines or shapes of various widths and spatial separation or line densities. The image of the target formed by an optical system is evaluated in order to determine the SFR of the optical system.

In one approach, determination of the SFR of the optical instrument by a contrast method is described. The contrast level between line pairs degrades as the separation and width of the line pairs decreases. The contrast level of various line pair widths and separations are measured. The optical resolution of the instrument is a measure of the contrast of the various line pairs and can be equated to as a measure of the optical system quality in terms of resolvable Line Pairs per millimeter separation or (LP/min). A function of the relationship between the contrast and the LP/mm separation is the Contrast Sensitivity Function (CSF) of the instrument. Once the CSF of the instrument is known, the MTF or % MTF of the optical system can be derived directly from a Contrast Sensitivity Function (CSF), as MTF=pi/4*CSF where CSF=C(f)/C(0). The CSF value therefore is the contrast ratio that is measured directly from the line pairs as contrast (C) at a specific spatial frequency C(f), with C(f) comprising:

$$C(f)=(I\text{peak}-I\text{valley})/(I\text{peak}+I\text{valley}) \qquad (2)$$

Where Ipeak and Ivalley are the intensities of the image generated by the spatial frequency mask 120. Ipeak is a measure the intensity of a bright image segment maxima and Ivalley is a measure of the intensity of a dark image segment adjacent the bright image segment minima of the mask at a specific location or spatial frequency along the test pattern or spatial frequency mask 120.

The value of the function C(f) is divided by the contrast at low spatial frequencies C(0) within the same test pattern scan, with C(0) comprising:

$$C(0)=(\text{avg}(I\text{white})-\text{avg}(I\text{dark}))/(\text{avg}(I\text{white})+\text{avg}(I\text{dark})) \qquad (3)$$

Where avg(Iwhite) and avg(Idark) are the average intensity values of low spatial frequency adjacent image segments within the test pattern. The intensity avg(Iwhite) is the average intensity of a bright image segment of the test pattern and avg(Idark) is the average intensity of an adjacent dark image segment of the test pattern or spatial frequency mask 120. It should be noted that averaging the bright and dark regions in effect compensates for any changes in gain during the data acquisition.

Alternatively, the MTF can be determined by evaluation of the spatial frequency content using a Fourier Transform (FT) or a Fast Fourier Transform (FFT) of a single image. The spatial frequency content can be determined from a Line Spread Function (LSF), Point Spread Function (PSF), of an Edge Response Function (ERF), or any vector representation of the spatial frequency mask 120. Regardless of the method of evaluation, the resultant function of interest is the spatial frequency response of the optical instrument 100.

The spatial frequency response of the optical measurement instrument 100 can be represented by:

$$y_{k,w} = \frac{1}{\sqrt{1^2 + (2\cdot\pi\cdot\text{Hz}_w\cdot RC)^2}} \cdot \sin(2\cdot\pi\cdot t_k\cdot\text{Hz}_w) \qquad (4)$$

The RC term is a low pass filter constant analogous for the interaction of particulate material of the sample material on the encoded light, together with the limit of resolution of the instrument system 100 without particulate matter present in, the sample. The given RC is first described with no turbidity present in the sample material. The $Hz_w$ term is the fundamental frequency. The w term is a frequency range variable and in some embodiments ranges from zero to m/2 and is the light encoded frequency content of the image. The $t_k$ term is the time in seconds of each sample or the sampling interval across the image. The k term is a range variable and can range from zero to m−1, where m is the number of samples.

The time-domain or edge response, represented above by $(y_{k,w})$, is converted into the frequency domain for further processing. The conversion is represented by:

$$Y^{(w)} = FFT(y^{(w)}) \quad (5)$$

The $(Y^{(w)})$ term is the frequency domain MTF response. The frequency domain MTF response can be processed through a summation comprising:

$$Y = \sum_w Y^{(w)} \quad (6)$$

The resulting frequency domain amplitudes Y can be obtained for maximum and minimum resolvable black and white regions. In this example, the w frequency range values have been chosen as 2 and 50 LP/mm. Other spatial frequency values (w) can be chosen according to the spatial frequency mask 120. The ratio of the content of high spatial frequency Y versus a low spatial frequency Y can be obtained. In this example, the ratio comprises:

$$\frac{|Y_{50}|}{|Y_2|} = 0.954104 \quad (7)$$

The resulting number, 0.954104 in this example, comprises a MTF turbidity measurement. This result represents a near absence of turbidity, i.e., it shows that the contrast for the high spatial frequency black and white regions (small bars) are about ninety-five percent of the contrast for the low spatial frequency black and white regions with no turbidity present.

Figure 5:
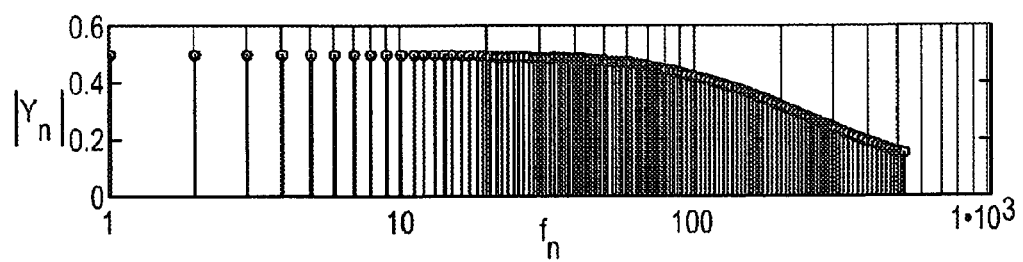
FIG. 5 is a graph of frequency domain amplitude values |Y| for a low turbidity example.

FIG. 5 is a graph of frequency domain amplitude values |Y| for a low turbidity example (i.e., the 95% MTF in the example above). The graph shows a relatively small and gradual loss in amplitude or contrast, |Y| versus spatial frequency $f_n$.

Figure 6:
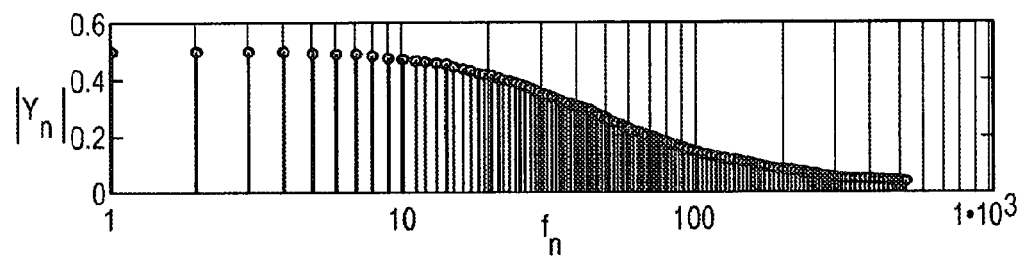
FIG. 6 is a graph of frequency domain amplitude values |Y| for a high turbidity example.

FIG. 6 is a graph of frequency domain amplitude values |Y| for a high turbidity example, such as where the RC term is increased in equation (4). The graph shows a relatively large and steep loss in contrast |Y| versus the spatial frequency $f_n$.

Figure 7:
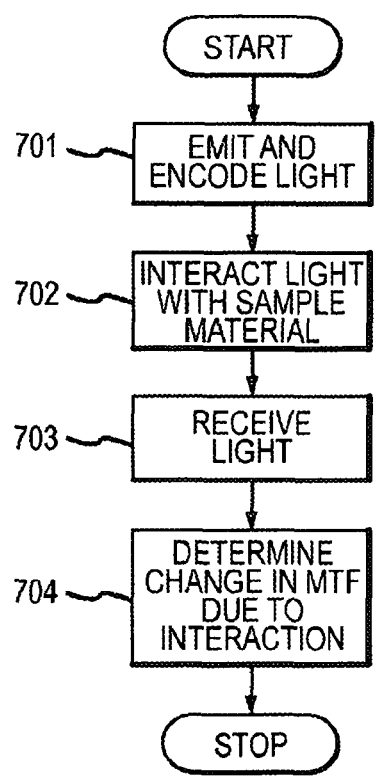
FIG. 7 is a flowchart of a spatial frequency optical measurement method according to an embodiment of the invention.

FIG. 7 is a flowchart 700 of a spatial frequency optical measurement method according to an embodiment of the invention. In step 701, light is emitted and encoded with spatial frequency information. The light is encoded with the spatial information by a spatial frequency mask, as previously discussed. The light propagates along a path through a sample material (or past, in the case of a solid surface sample material). Alternatively, the emitted light can be reflected from the spatial frequency mask to encode spatial information on the light.

In step 702, the light is interacted with the sample material. The turbidity of the sample material (or surface characteristics of the sample material) will confuse the spatial frequency information, as previously discussed. The light can be interacted with the sample material by directing the light through the sample material one or more times. Alternatively, the light can be reflected from the sample material one or more times.

In step 703, a light receiver of the instrument receives the light as an image of the spatial frequency mask. Various optical components can be used to direct and form the image. The light therefore has passed through, passed by, or has been reflected from spatial frequency mask and the sample material. The light can pass through the sample material multiple times, if beneficial, such as when the sample material has a relatively low turbidity so as to effectively increase the interaction of the encoded light with the sample material. The resulting image is used to generate a MTF of the instrument.

In step 704, a change in the MTF is determined. The MTF response varies according to the particulate concentration within the sample material, as related to changes in the spatial frequency content of the image. The change in the MTF is determined in one embodiment by comparison to a MTF for a sample material bearing no suspended particulates (or by a comparison to a MTF for no sample material in the instrument). Determining the change in MTF can use frequency processing methods or contrast methods, as previously discussed. The processing can determine a presence or absence of particles, a turbidity measurement, and/or a particulate concentration, for example.

Figure 8:
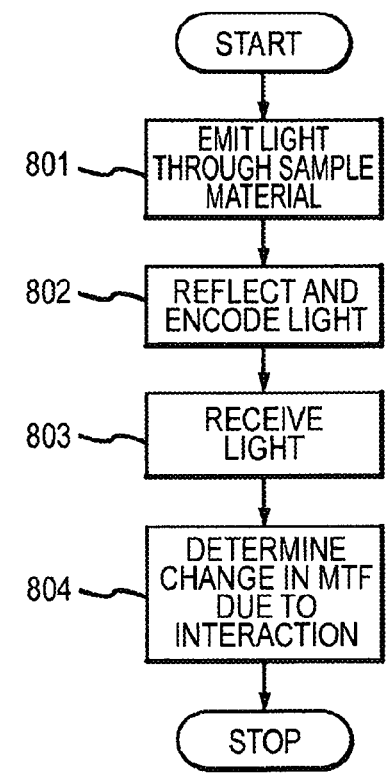
FIG. 8 is a flowchart of a spatial frequency optical measurement method according to an embodiment of the invention.

FIG. 8 is a flowchart 800 of a spatial frequency optical measurement method according to an embodiment of the invention. In step 801, light is interacted with a sample material. The light has not been encoded with spatial frequency information. The light propagates along a path through a sample material (or past, in the case of a solid surface sample material). The light can be interacted with the sample material more than once, as previously discussed.

In step 802, the interacted light is reflected and encoded with spatial frequency information. The light in some embodiments is encoded with the spatial information by a reflective spatial frequency mask that reflects a portion of the impinging light, as previously discussed. The reflected encoded light in some embodiments may again pass through the sample material. The light may have already been confused by the interaction with the sample material.

In step 803, a light receiver of the instrument receives the light as an image of the spatial frequency mask, as previously discussed.

In step 804, a change in the MTF is determined, as previously discussed.

Figure 9:
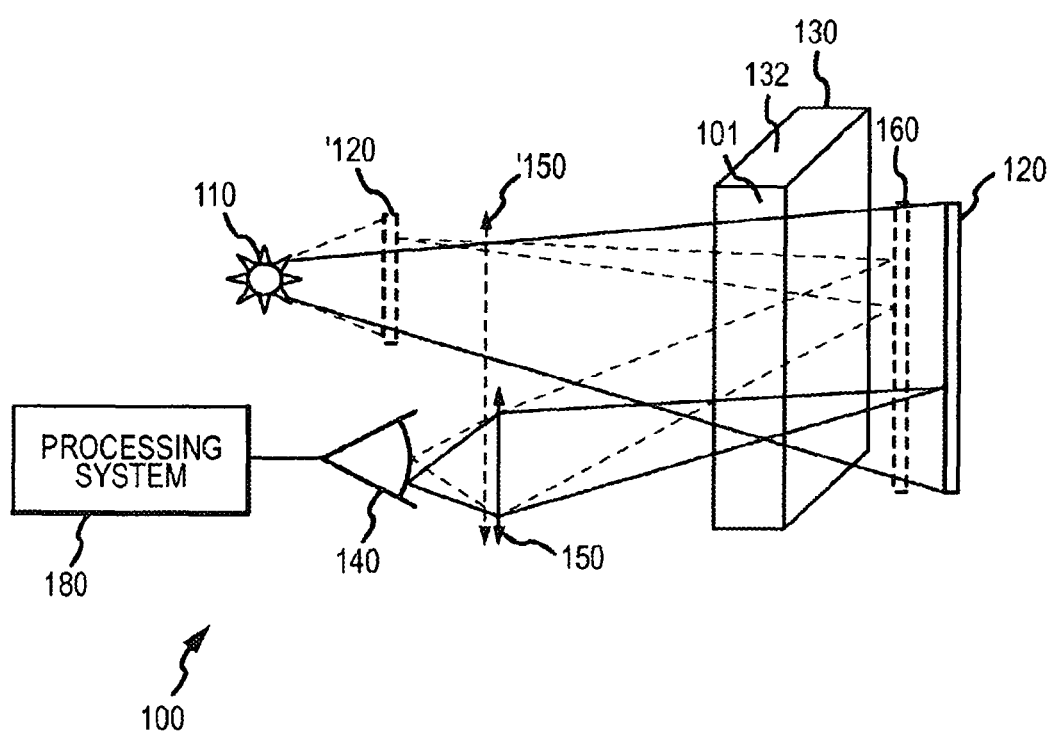
FIG. 9 shows the spatial frequency optical measurement instrument according to an embodiment of the invention.

FIG. 9 shows the spatial frequency optical measurement instrument 100 according to an embodiment of the invention. Components in common with FIG. 2 share reference numbers. In this embodiment, the light source 110 is positioned beside the light receiver 140. Light from the light source 110 is emitted along a first light path that includes the sample material 132. The instrument 100 in this embodiment includes a reflective spatial frequency mask 120. In addition, the illuminating first light path may also include an optic 150' for both illuminating the spatial frequency mask 120 and for forming an image along a second light path through the sample material 132. Light propagating through the sample material 132 is reflected from the spatial frequency mask 120. Consequently, the reflective spatial frequency mask 120 comprises a series of (spatially varying) light reflecting and non-reflecting regions that encode the spatial frequency information. The second light path can further include an optic 150 for forming the resulting image.

The reflective surface 160 may be any shape of reflective surface. The reflective surface 160 may include a non-reflective surface, for example a second-surface mirror, so long as the reflective surface does not adversely contribute to loss or corruption of the spatial frequency information encoded within the reflected light.

Alternatively, a spatial frequency mask 120' can be positioned along the first optical path. Consequently, the spatial frequency mask 120' is positioned prior to the sample material 132, the reflective surface 160, and the image forming optic 150.

Figure 10:
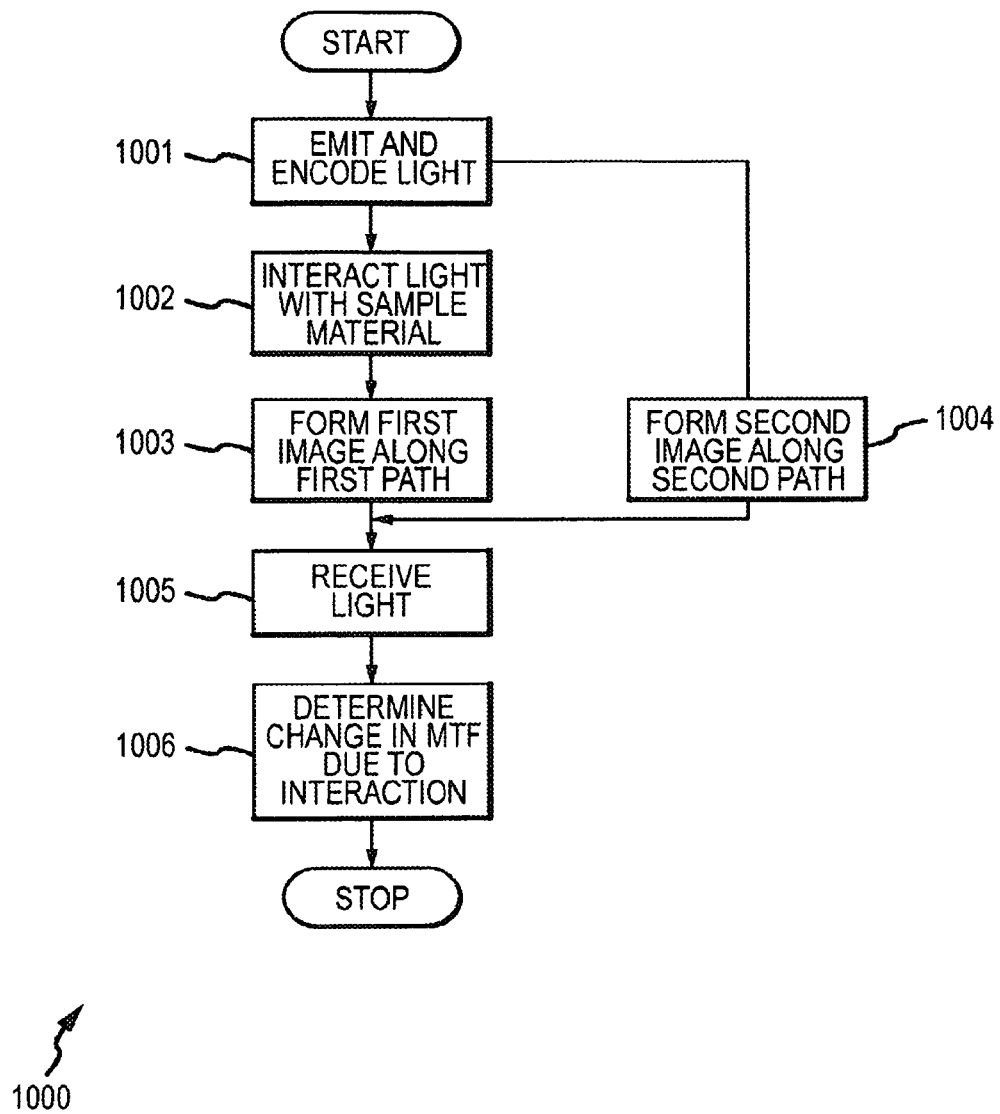
FIG. 10 is a flowchart of an embodiment that has a first light path for the encoded light to form an image that has propagated through the sample material and a second light path that does not include the sample material.

FIG. 10 is a flowchart of an embodiment that has a first light path for the encoded light to form an image that has propagated through the sample material and a second light path that does not include the sample material. In step 1001, light is emitted and is encoded by a mask that includes spatial frequency information. The emitted and encoded light comprises two light paths. The two light paths can be generated in any manner.

In step 1002, a first light emitted along a first light path interacts with the sample material. The encoded first light is confused by the interaction and some of the spatial frequency information is lost due to the interaction.

In step 1003, a first image is formed using the first light. The first image includes the confused spatial frequency information.

In step 1004 a second light emitted along a second light path does not include or interact with the sample material. A second image is formed using the second light. The second image includes the unchanged spatial frequency information. This unchanged spatial frequency information can be used as a reference.

In step 1005, the first image and the second image are received. Any manner of optical components can process and/or enhance the image. In addition, the received first and second images can be processed in order to extract the spatial frequency information.

In step 1006, a change in the MTF is determined. The change can be determined by comparison of the sample-modified (i.e., confused) spatial frequency information to the spatial information unmodified by interaction of the encoded light with the sample material.

Figure 11:
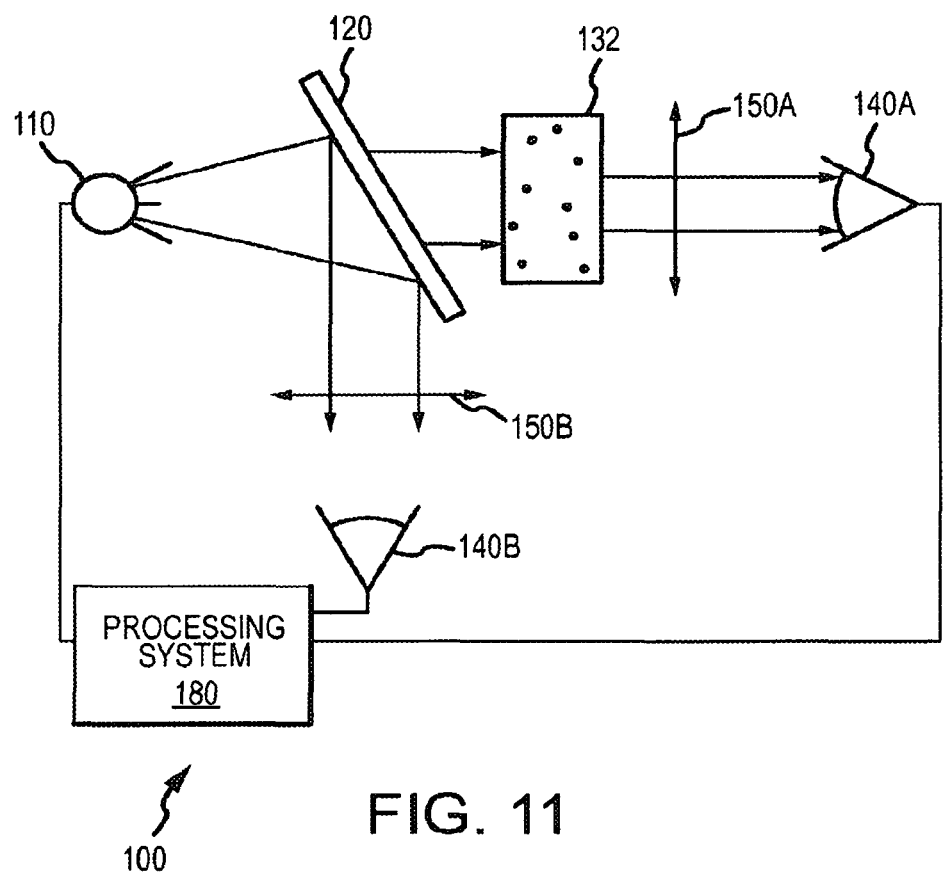
FIG. 11 shows the spatial frequency optical measurement instrument according to an embodiment of the invention.

FIG. 11 shows the spatial frequency optical measurement instrument 100 according to an embodiment of the invention. In this embodiment, the instrument 100 includes both a first light path and a second light path. Light that is emitted along a first light path is encoded with the spatial frequency information, as previously discussed, by being transmitted through openings or clear areas of the spatial frequency mask 120. This encoded light continues traveling toward the first light receiver 140A. At the same time, a portion of the light from the light source 110 is reflected by opaque or reflecting surfaces of the spatial frequency mask 120 along a second light path toward the second light receiver 140B. Clear areas of the spatial frequency mask 120 transmit encoded light to the sample material 132 whereas reflecting areas of the encoding mask reflect the encoded light on a path that does not include the sample material. As previously discussed, light that interacts with the sample material 132 is confused through interaction with the particles of the sample material 132. Images are formed by the imaging forming optics 150A and 150B onto the respective light receivers 140A and 140B. The processing system 180 evaluates changes to the content or organization of the spatial frequency information by comparison of the image formed from the sample-modified light to the image formed with light that did not interact with the sample material 132. The image formed by unmodified light is used as a reference and can be used to compensate for image degradation due. In this way manufacturing tolerances of the optical components of a spatial frequency instrument 100 can be loosened and still provide like performance between different instruments.

Figure 12:
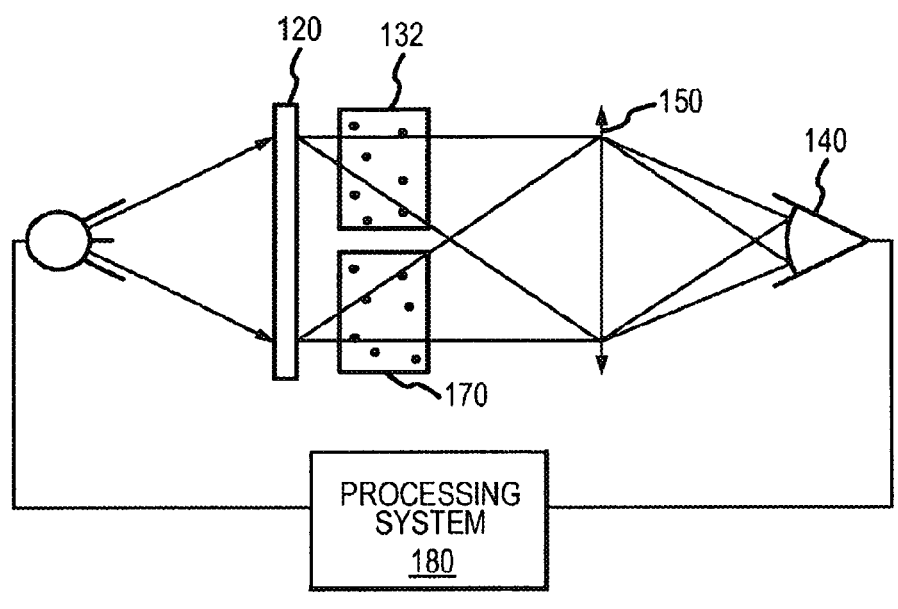
FIG. 12 shows the spatial frequency optical measurement instrument according to an embodiment of the invention.

FIG. 12 shows the spatial frequency optical measurement instrument 100 according to an embodiment of the invention. The spatial frequency optical measurement instrument 100 in this embodiment further includes a standard material(s) 170 that is located adjacent to the sample material 132. The standard material(s) 170 provides a material of unchanging interaction with the encoded light for the purpose of verification of performance. The standard material(s) 170 therefore comprises a self-calibration and/or reference means.

In operation, light from the light source 110 is encoded by light passing through, past, or reflected from the spatial frequency mask 120. The encoded light is subsequently interacted with both the standard material 170 and the sample material 132. An image of the spatial frequency mask 120 is formed by the image forming optic 150 at the light receiver 140. The image is comprised of encoded light, portions of which have exclusively interacted with the standard material 170 and portions that have exclusively interacted with the sample material 132. The standard result does not vary in relation to the sample material 132 and can therefore be used to verify the performance and/or can be used to self-calibrate the instrument 100. Further, the standard result can be used as a reference against which the encoded, confused spatial frequency image from the sample material 132 can be compared and which enables interpolation and/or extrapolation of results by the processing system 180.

Alternately, the spatial frequency content of the spatial frequency mask 120 may be altered in whole or in part in order to provide a reference and/or self-calibration means without need of any standard material. In application, the portions of the spatial frequency mask 120 having different spatial frequency information are exclusively imaged with no sample material 132 present or with no interaction of the encoded light or radiant energy. For example, the sample material 132 can comprise a segmented sample, wherein a portion of the sample 132/sample compartment 130 is clear or free of interaction with encoded light. As a result, the non-interacted light generates an instrument response of a reference value with a known spatial frequency content that is in no relation to the sample material 132. In another alternative, the emitted light can be split into at least two paths, wherein one portion can be directed to the light receiver 140 without passing through the sample material 132.

The detailed embodiments disclosed herein, the spatial frequency optical measurement instrument and method may be accomplished in a variety of forms without departing from the scope or intent of this invention by those skilled in the art and is not limited to the disclosed embodiments but should be defined by the claims which follow.

What is claimed is:

1. A spatial frequency optical measurement instrument, comprising:
 a spatial frequency mask positioned in a light path and configured to encode light with spatial frequency information;
 a light receiver positioned to receive the light encoded with the spatial frequency information, wherein the light encoded with the spatial frequency information has been interacted with a sample material; and a processing system coupled to the light receiver and configured to determine a change in the spatial frequency information due to the interaction of the light with the sample material;

wherein the processing system determines one or more of:

a particulate concentration in the sample material; and a surface characteristic of the sample material.

2. The spatial frequency optical measurement instrument of claim 1, wherein the processing system determines a surface characteristic of the sample via comparing the light encoded with the spatial frequency information and that has been interacted with the sample material to a predetermined contrast standard.

3. The spatial frequency optical measurement instrument of claim 1, wherein the processing system determines a particulate concentration of the sample material via comparing the light encoded with the spatial frequency information and that has been interacted with the sample material to a predetermined particulate concentration image.

4. A spatial frequency optical measurement method, comprising:

encoding light with spatial frequency information;

interacting the light with a sample material; and operating a processing system to determine a change in the spatial frequency information due to the interaction of the light with the sample material in order to determine one or more of:

a particulate concentration in the sample material; and a surface characteristic of the sample material.

5. The spatial frequency optical measurement method of claim 4, wherein the processing system determines a surface characteristic of the sample via comparing the light encoded with the spatial frequency information and that has been interacted with the sample material to a predetermined contrast standard.

6. The spatial frequency optical measurement method of claim 4, wherein the processing system determines a particulate concentration of the sample material via comparing the light encoded with the spatial frequency information and that has been interacted with the sample material to a predetermined particulate concentration image.

* * * * *